United States Patent
Kaul et al.

(10) Patent No.: US 6,214,989 B1
(45) Date of Patent: Apr. 10, 2001

(54) TRIPHENDIOXAZINE PIGMENTS

(75) Inventors: Bansi Lal Kaul, Biel-Benken (CH); Bruno Piastra, Huningue (FR)

(73) Assignee: Clariant International, Ltd. Muttenz (CH)

( * ) Notice: Subject to any disclaimer, the term of this patent is extended or adjusted under 35 U.S.C. 154(b) by 0 days.

(21) Appl. No.: 09/275,566

(22) Filed: Mar. 24, 1999

(30) Foreign Application Priority Data

Mar. 26, 1998  (CH) .................................................... 0717/98

(51) Int. Cl.[7] .................... C07D 498/00; C07D 265/34
(52) U.S. Cl. .................... 544/74; 54/14; 54/76; 54/99
(58) Field of Search .................. 544/74, 75, 76, 544/14, 99; 8/506

(56) References Cited

U.S. PATENT DOCUMENTS

| 4,395,545 | 7/1983 | Adam et al. ............................. 544/74 |
| 4,750,935 | 6/1988 | Prochaska et al. ..................... 106/20 |
| 4,876,342 | 10/1989 | Pedrazzi ................................. 544/14 |
| 5,041,629 | 8/1991 | Herd et al. ............................ 562/453 |
| 5,126,481 | 6/1992 | Herd et al. ............................ 562/37 |
| 5,484,943 | 1/1996 | Zambounis et al. .................. 548/453 |
| 5,616,725 | 4/1997 | Zambounis et al. .................. 548/453 |

FOREIGN PATENT DOCUMENTS

| 4442291 | 6/1995 | (DE) . |
| 0014678 | 8/1980 | (EP) . |
| 0184711 | 6/1986 | (EP) . |
| 0271781 | 6/1988 | (EP) . |
| 0355598 | 2/1990 | (EP) . |
| 0889046 | 1/1999 | (EP) . |
| 2284427 | 6/1995 | (GB) . |

OTHER PUBLICATIONS

European Search Report.
Derwent Patent Family Report and/or Abstracts.

*Primary Examiner*—Mukund J. Shah
*Assistant Examiner*—Sudhaker B. Patel
(74) *Attorney, Agent, or Firm*—Susan S. Jackson; Scott E. Hanf

(57) ABSTRACT

Carbamate group-containing triphendioxazine compounds of the formula (I)

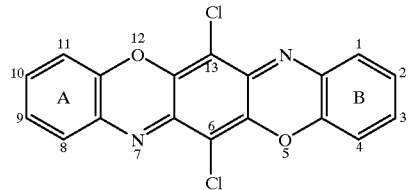

(I)

where the nuclei designated A and B, as defined in claim 1, contain fused-on rings and $R_1$, $R_2$ and $R_3$ have the meanings specified in claim 1, are good pigments and are convertible into the corresponding triphendioxazine pigments without carbamate groups.

10 Claims, No Drawings

TRIPHENDIOXAZINE PIGMENTS

The present invention relates to novel triphendioxazine compounds containing carbamate groups, their preparation and their use as pigments and also as pigment precursors which are readily convertible into the corresponding pigments.

The present invention provides novel carbamate group-containing triphendioxazine compounds which not only can be used as pigments, but are also readily convertible into the corresponding triphendioxazine pigments without carbamate groups and accordingly clear the way to unexpected applications. Including compounds having N-alkoxycarbonyl groups whose alkyl radicals are branched at the carbon which is attached to the oxygen.

The present invention accordingly provides compounds of the formula (I)

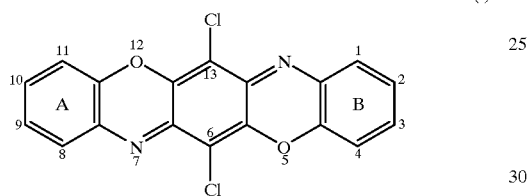

(I)

in which the nuclei designated A and B independently of each other comprise annelated rings which are fused on linearly, in 2,3- and 9,10-position, or angularly, in 1,2- and 8,9 or in 3,4- and 10,11-position, to feature the complementary members selected from the group consisting of the moieties (1) to (11)

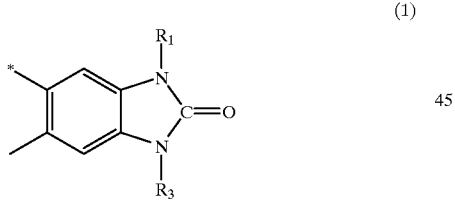

(1)

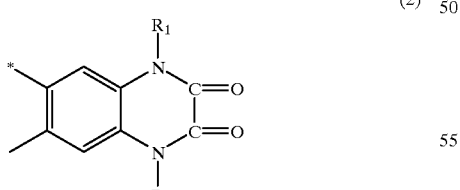

(2)

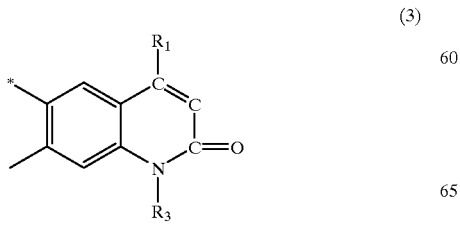

(3)

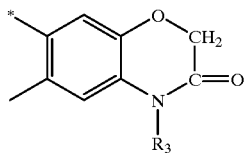

(4)

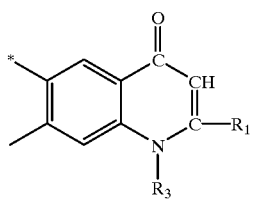

(5)

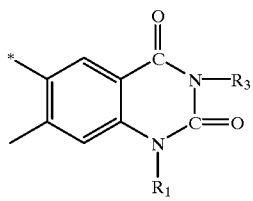

(6)

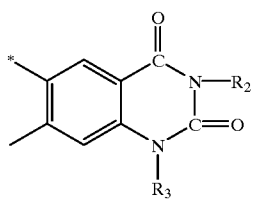

(7)

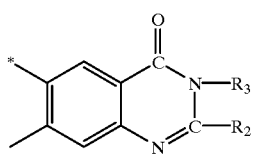

(8)

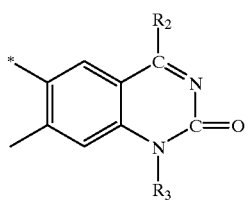

(9)

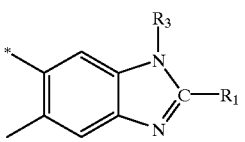

(10)

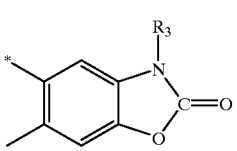

(11)

wherein $R^1$ is hydrogen, $C_{1-8}$alkyl, unsubstituted phenyl or phenyl which is mono- or poly- substituted by radicals selected from the group consisting of halogen, nitro groups, $C_{1-8}$alkyl and $C_{1-2}$alkoxy, preferably chlorine or $C_{1-4}$alkyl, $R_2$ is hydrogen, $C_{1-8}$alkyl, unsubstituted phenyl, an amino group or phenyl which is mono- or poly-substituted by radicals selected from the group consisting of halogen, nitro groups, $C_{1-8}$alkyl and $C_{1-2}$alkoxy, preferably chlorine or $C_{1-4}$alkyl;

and the bond designated with an * leads to the nitrogen atom and the angular molecules in 3- and 10-position or in 2- and 9-position may each bear a $C_{1-2}$alkoxy group, the radicals $R_3$ are selected from the group consisting of the formulae (II), (III) and (IV)

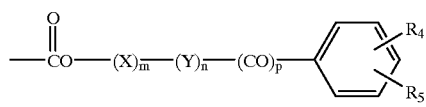
(II)

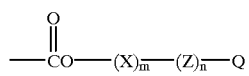
(III)

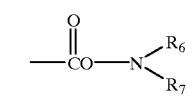
(IV)

wherein m, n and p are independently of each other zero or 1;

X is $C_{1-4}$alkylene or $C_{2-8}$alkenylene;

Y is a group —V—$(CH_2)_q$—;

Z is a group —V—$(CH_2)_r$—;

V is $C_{3-6}$cycloalkylene;

q is an integer from 1 to 6; and r is an integer from 0 to 6, $R_4$ and $R_5$ are independently hydrogen, $C_{1-6}$alkyl, $C_{1-4}$alkoxyl, halogen, —CN, —$NO_2$, unsubstituted phenyl or phenoxy or phenyl or phenoxy substituted by $C_{1-4}$alkyl, $C_{1-4}$alkoxyl or halogen;

Q is hydrogen, —CN, $Si(R_4)_3$, a group $C(R_8)(R_9)(R_{10})$, wherein $R_8$, $R_9$ and $R_{10}$ are halogen, a group

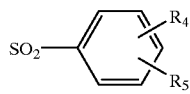

in which $R_4$ and $R_5$ are as defined above, a group $SO_2$—$R_{11}$ or $SR_{11}$, wherein $R_{11}$ is $C_{1-4}$alkyl, a group $CH(R_{12})_2$, wherein $R_{12}$ is unsubstituted phenyl or phenyl substituted by $C_{1-4}$alkyl, $C_{1-4}$alkoxyl or halogen, or a group of the formula

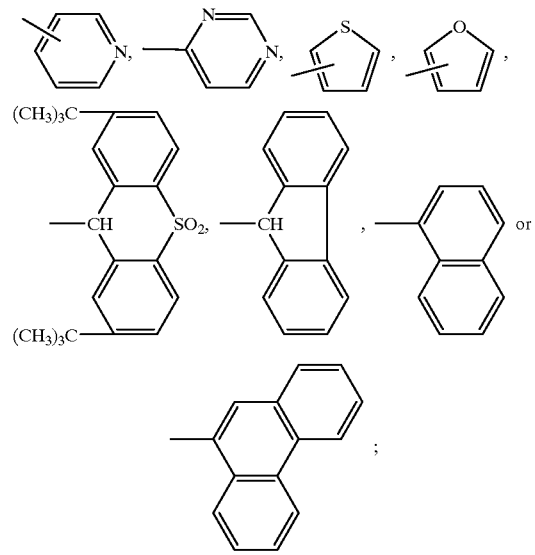

$R_6$ and $R_7$ are independently of each other hydrogen, $C_{1-18}$alkyl, a group of the formula

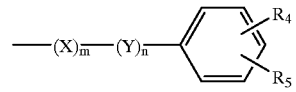

in which

X, Y, $R_4$, $R_5$, m and n are as defined above, or $R_6$ and $R_7$ together with the nitrogen atom to which they are bonded form a pyrrolidinyl, piperidinyl or morpholinyl radical, with the proviso that, when $R_3$ is a group of the formula (III), Q is hydrogen and n is zero, then m shall be 1 and X shall be a $C_{2-14}$alkylene or $C_{2-8}$alkenylene group which is branched at the carbon which is attached to the oxygen.

If X denotes $C_{1-4}$alkylene X is a straight-chain or branched alkylene, for example methylene, dimethylene, trimethylene, 1-methyl-methylene, 1,1-dimethyl-methylene, 1,1-dimethyl-dimethylene, 1,1-dimethyl-trimethylene, 1-ethyl-dimethylene, 1-ethyl-1-methyl-dimethylene, tetramethylene, 1,1-dimethyl-tetramethylene, 2,2-dimethyl-trimethylene, hexamethylene, decamethylene, 1,1-dimethyl-decamethylene, 1,1-diethyl-decamethylene or tetradecamethylene.

If X stands for $C_{2-8}$-alkenylene X is a straight-chain or branched alkenylene, for example vinylene, allylene, methallylene, 1-methyl-2-butenylene, 1,1-dimethyl-3-butenylene, 2-butenylene, 2-hexenylene, 3-hexenylene or 2-octenylene.

Is any substitutent halogen then it is for example iodine, fluorine, especially bromine and preferably chlorine;

$C_{1-6}$Alkyl is for example methyl, ethyl, n-propyl, isopropyl, n-butyl, sec-butyl, tert-butyl, n-amyl, tert-amyl, hexyl and $C_{1-8}$alkyl is additionally for example heptyl, octyl, 2-ethylhexyl, nonyl, decyl, dodecyl, tetradecyl, hexadecyl or octadecyl;

$C_{1-4}$Alkoxy signifies for example methoxy, ethoxy, n-propoxy, isopropoxy, butyloxy, and $C_{1-8}$alkoxy is additionally for example hexyloxy, decyloxy, dodecyloxy, hexadecyloxy or octadecyloxy;

$C_{1-18}$Alkylmercapto is for example methylmercapto, ethylmercapto, propylmercapto, butylmercapto, octylmercapto, decylmercapto, hexadecylmercapto or octadecylmercapto;

$C_{1-18}$Alkylamino is for example methylaminio, ethylamino, propylamino, hexylamino, decylamino, hexadecylamino or octadecylamino.

$C_{5-6}$Cycloalkyl is for example cyclopentyl and especially cyclohexyl.

$C_{3-6}$Cycloalkylene is for example cyclopropylene, cyclopentylene and especially cyclohexylenes.

In preferred compounds of the formula (I), the moieties

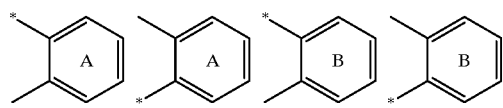

preferably correspond to the formulae (a) to (p)

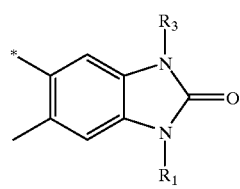
(a)

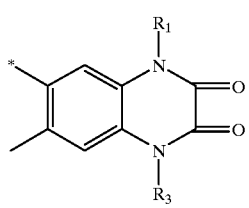
(b)

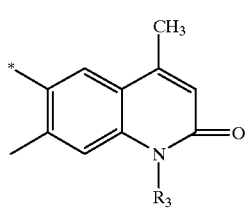
(c)

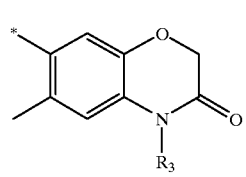
(d)

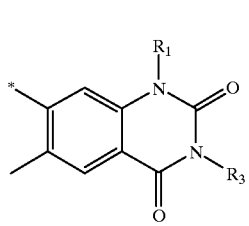
(e)

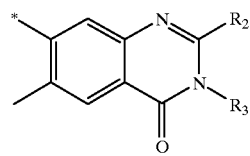
(f)

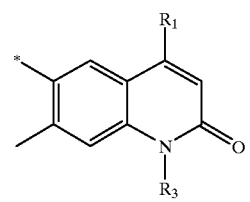
(g)

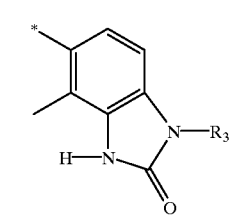
(h)

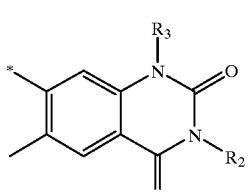
(i)

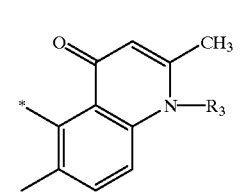
(j)

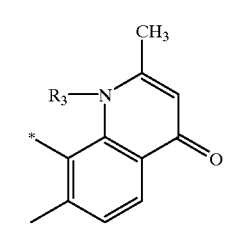
(k)

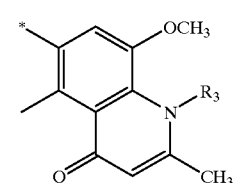
(l)

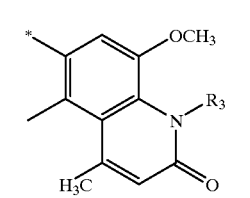
(m)

-continued (n)

*—[benzimidazole with OCH3, CH3 substituents, R3—N, CH3]

(o)

*—[benzimidazolone with OCH3, CH3 substituents, R3—N, NH, =O]

(p)

*—[quinolinone with H3C, CH3 substituents, N—R3, =O]

Preferred are compounds of the formula (I) in which $R_3$ represents a group of the formula (V), (VI) or (IV)

(V)

$$-\overset{O}{\underset{}{C}}-(X)_{\overline{m}}-\underset{R_5}{\overset{R_4}{\diagup\!\!\!\diagdown}}$$

(VI)

$$-\overset{O}{\underset{}{C}}-X-Q$$

or (IV)

$$-\overset{O}{\underset{}{C}}-N\underset{R_7}{\overset{R_6}{\diagup\!\!\!\diagdown}}$$

wherein m is zero or 1,

X is $C_{1-4}$alkylene or $C_{2-5}$alkenylene, $R_4$ and $R_5$ are independently of each other hydrogen, $C_{1-4}$alkyl, methoxy, chlorine or —$NO_2$, and Q is hydrogen, CN, $CCl_3$, a group $$SO_2-\underset{R_5}{\overset{R_4}{\diagup\!\!\!\diagdown}}$$

—$SO_2CH_3$ or $SCH_3$, $R_6$ and $R_7$ are independently of each other hydrogen, $C_{1-4}$alkyl or a group $$-(X)_{\overline{m}}-\underset{R_5}{\overset{R_4}{\diagup\!\!\!\diagdown}}$$

or $R_6$ and $R_7$ form together a piperidinyl radical, with the proviso that, when $R_3$ is a group of the formula (VI) and Q is hydrogen, then X shall be a group $$-\underset{CH_3}{\overset{CH_3}{\overset{|}{C}}}-,\quad -\underset{CH_3}{\overset{CH_3}{\overset{|}{C}}}-CH_2-,\quad -\underset{CH_3}{\overset{CH_3}{\overset{|}{C}}}-CH=CH_2-\text{ or}$$

$$-\underset{CH_3}{\overset{}{C}}=CH-$$

especially if the radical $R_3$ signifies a group selected from the group containing of the following formulae $$-\overset{O}{\underset{}{C}}O-CH_2-\text{Ph}\,,\quad -\overset{O}{\underset{}{C}}O-C(CH_3)_3,$$

$$-\overset{O}{\underset{}{C}}O-CH_2-\text{Py}\,,$$

$$-\overset{O}{\underset{}{C}}O-CH_2-SO_2-\text{Ph} \quad \text{and}$$

$$-\overset{O}{\underset{}{C}}O-N\text{(piperidinyl)}$$

The invention further provides a process for preparing triphendioxazine compounds of the formula (I), characterized in that a compound of the formula (VII)

(VII)

[Triphendioxazine structure with positions numbered 1-13, rings A and B, two Cl substituents at positions 6 and 13, O at 5,12, N at 7,14]

wherein the nuclei designated A and B have the same meaning as in formula (I) but $R_3$ is hydrogen, is reacted in the desired molar ratio with a dicarbonate of the formula (VIII)

$$R_3-O-R_3 \qquad (VIII)$$

or with a trihaloacetic ester of the formula (IX)

$$(R_{13})_3C-R_3 \qquad (IX)$$

or with a 1:1 mixture of a dicarbonate of the formula (VIII) and a dicarbonate of the formula (X)

$$R'_3\text{---}O\text{---}R'_3 \quad (X)$$

or with a 1:1 mixture of a trihaloacetic ester of the formula (IX) and a trihaloacetic ester of the formula (XI)

$$(R_{13})_3C\text{---}R'_3 \quad (XI)$$

or with an azide of the formula (XII)

$$R_3N_3 \quad (XII)$$

which may also be used in a 1:1 mixture with $$R'_3N_3 \quad (XIII)$$

or with a carbonate of the formula (XIV)

$$R_3\text{---}OR_{14} \quad (XIV)$$

which may also be used in a 1:1 mixture with $$R'_3\text{---}OR_{14} \quad (XV)$$

or with an alkylideneiminooxyformic ester of the formula (XVI)

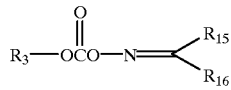
(XVI)

which may also be used in a 1:1 mixture with

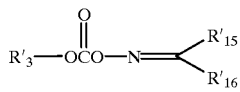
(XVII)

wherein $R_3$ is as defined above and $R'_3$ has a meaning of $R_3$ which is different from $R_3$, $R_{13}$ is chlorine, fluorine or bromine, $R_{14}$ is $C_{1-4}$alkyl or unsubstituted phenyl or phenyl substituted by halogen, $C_{1-4}$alkyl, $C_{1-4}$alkoxyl or —CN, $R_{15}$ is —CN or —COOR$_{14}$, and $R'_{15}$ has a meaning of $R_{15}$ which is different from $R_{15}$, and $R_{16}$ is unsubstituted phenyl or phenyl substituted by halogen, $C_{1-4}$alkyl, $C_{1-4}$alkoxyl or —CN, and $R'_{16}$ has a meaning of $R_{16}$ which is different from $R_{16}$, in an aprotic organic solvent in the presence of a base as catalyst, advantageously at temperatures between 0 and 200° C., preferably between 10 and 100° C., for 2 to 48 hours.

Preferably, the compound of the formula (VII) is reacted with a dicarbonate of the formula (VIII) or with a 1:1 mixture of a dicarbonate of the formula (VIII) and a dicarbonate of the formula (X).

Compounds of the formula (VII), dicarbonates of the formulae (VIII) and (X), trihaloacetic esters of the formulae (IX) and (XI), azides of the formulae (XII) and (XIII), carbonates of the formulae (XIV) and (XV) and alkylideneiminooxyformic esters of the formulae (XVI) and (XVII) are known substances. Should any be novel nonetheless, they can be prepared in analogy to commonly known methods.

The necessary molar ratio between triphendioxazine pigments of the formula (VII) and the compounds of the formulae (VIII) to (XVII) depends on the radicals $R_3$ and $R'_3$ to be introduced. Advantageously, however, the compounds of the formulae (VIII) to (XVII) are used in 2- to 10-fold excess.

Examples of suitable solvents are ethers, such as tetrahydrofuran or dioxane, or glycol-ethers, such as ethylene glycol methyl ether, ethylene glycol ethyl ether, diethylene glycol monomethyl ether or diethylene glycol monoethyl ether, further dipolar aprotic solvents, such as acetonitrile, benzonitrile, N,N-dimethylformamide, N,N-dimethylacetamide, nitrobenzene, N-methylpyrrolidone, halogenated aliphatic or aromatic hydrocarbons, such as trichloroethane, benzene or alkyl-, alkoxy- or halogen-substituted benzene, such as toluene, xylene, anisole or chlorobenzene or aromatic N-heterocycles, such as pyridine, picoline or quinoline. Preferred solvents are for example tetrahydrofuran, N,N-dimethylformamide, N,N-dimethylacetamide or N-methylpyrrolidone. The solvents mentioned can also be used as mixtures. Advantageously, 5–10 parts by weight of solvent are used per 1 part by weight of the reaction participants.

Bases suitable for use as catalyst are for example the alkali metals themselves, such as lithium, sodium or potassium, as well as their hydroxides or carbonates, or alkali metal amides, such as lithium amide, sodium amide or potassium amide, or alkali metal hydrides, such as lithium hydride, sodium hydride or potassium hydride, or alkaline earth or alkali metal alcoholates which are derived especially from primary, secondary or tertiary aliphatic alcohols having 1 to 10 carbon atoms, for example lithium, sodium or potassium methylate, ethylate, n-propylate, isopropylate, n-butylate, sec-butylate, tert-butylate, 2-methyl-2-butylate, 2-methyl-2-pentylate, 3-methyl-3-pentylate, 3-ethyl-3-pentylate, and further organic aliphatic, aromatic or heterocyclic N-bases, including for example diazabicyclooctene, diazabicycloundecene and 4-methylaminopyridine and trialkylamines, for example trimethyl- or triethyl-amine. It is also possible to use mixtures of the afore-mentioned bases.

Preferred are the organic N-bases, for example diazabicyclooctene, diazabicycloundecene and particularly 4-dimethylaminopyridine.

The reaction is preferably carried out at temperatures between 10 and 100° C., particularly between 14 and 40° C., and at atmospheric pressure.

The compounds according to the invention are suitable as pigments or fluorescent dyes for the mass coloration of macromolecular organic material.

Examples of suitable macromolecular organic materials which can be colored with the compounds of the formula (I) according to the invention are vinyl polymers, for example polystyrene, poly-α-methylstyrene, poly-p-methylstyrene, poly-p-hydroxystyrene, poly-p-hydroxyphenyistyrene, polymethyl acrylate, polyacrylamide, as well as the corresponding methacrylic compounds, polymethyl maleate, polyacrylonitrile, polymethacrylonitrile, polyvinyl chloride, polyvinyl fluoride, polyvinylidene chloride, polyvinylidene fluoride, polyvinyl acetate, polymethyl vinyl ether, and polybutyl vinyl ether; novolak resins derived from C$_{1-6}$aldehydes, for example formaldehyde and acetaldehyde, and a bicyclic, preferably monocyclic, phenol, which is optionally substituted by one or two C$_{1-9}$alkyl groups, one or two halogen atoms or a phenyl ring, for example o-, m- or p-cresol, xylene, p-tert-butylphenol, o-, m- or p-nonylphenol, p-chlorophenol or p-phenylphenol, or a compound having more than one phenolic group, for example resorcinol, bis(4-hydroxyphenyl)methane or 2,2-bis(4-hydroxyphenyl)propane; polymers derived from maleimide and/or maleic anhydride, for example copolymers of maleic anhydride and styrene; polyvinylpyrrolidone, biopolymers and derivatives thereof, for example cellulose, starch, chitin, chitosan, gelatin, zein, ethylcellulose, nitrocellulose, cellulose acetate and cellulose butyrate; natural resins and synthetic resins, for example rubber, casein, silicone and silicone resins, ABS, urea- and melamine-formaldehyde resins, alkyd resins, phenolic resins, polyamides, polyimides, polyamide/imides, polysulfones, polyether sulfones, polyphenylene oxides, polyurethanes, polyureas, polycarbonates, polyarylenes, polyarylene sulfides, polyepoxides, polyolefins and polyalkadienes. Preferred macromolecular organic materials are for example cellulose ethers and esters, such as ethylcellulose and nitrocellulose, cellulose acetate or cellulose butyrate, natural resins or synthetic resins, such as polymerization or condensation resins, such as aminoplasts, particularly urea- and melamine-formaldehyde resins, alkyd resins, phenoplasts, polycarbonates, polyolefins, polystyrene, polyvinyl chloride, polyamides, polyurethanes, polyesters, ABS, polyphenylene oxides, rubber, casein, silicone or silicone resins, individually or in mixtures.

The macromolecular organic compounds mentioned can be present individually or in mixtures as plastic masses, melts or in the form of spinning solutions, coatings, paints or printing inks. Depending on the intended use, it is advantageous to use the triphendioxazine compounds according to the invention as toners or in the form of a preparation.

The triphendioxazine compounds according to the invention are particularly useful for the mass coloration of polyesters, polyvinyl chloride and especially polyolefins, such as polyethylene and polypropylene, and ABS, as well as of coatings, and also of powder coatings, printing inks and paints.

Based on the macromolecular organic material to be colored, the triphendioxazine compounds according to the invention can be used in an amount of 0.01 to 30% by weight, preferably of 0.1 to 10% by weight.

The macromolecular organic substances are colored with the triphendioxazine compounds according to the invention for example by mixing the triphendioxazine pigment, optionally in the form of masterbatches, into these substrates using roll mills, mixing apparatus or grinding apparatus. The colored material is then brought into the desired final form according to processes known per se, such as calendering, pressing, extrusion, brushing, casting or injection molding. It is frequently desired, for the manufacture of nonrigid moldings or for reducing their brittleness, to incorporate plasticizers into the macromolecular compounds prior to molding. Examples of useful plasticizers are esters of phosphoric acid, phthalic acid or sebacic acid. Plasticizers can be incorporated into the polymers before or after incorporation of the triphendioxazine pigments according to the invention. To obtain various shades, it is further possible to add to the macromolecular organic substances, in addition to the triphendioxazine pigment according to the invention, also fillers or other color-conferring constituents such as white, color or black pigments, in arbitrary amounts.

To color coatings, paints and printing inks, the macromolecular organic materials and the triphendioxazine compounds according to the invention, optionally together with additives, such as fillers, pigments, siccatives or plasticizers, are finely dispersed or dissolved in a common organic solvent or solvent mixture. One way of accomplishing this is to disperse or dissolve the individual components or several together and only then to combine all components.

In colorings, for example of polyvinyl chloride or polyolefins, the triphendioxazine compounds according to the invention distinguish themselves by their good general properties, such as good migration, light and weather stability.

The quite unexpected ease with which the compounds according to the invention, even in the substrate in which they have already been incorporated, can be converted into the corresponding pigments of the formula (VII) is of great importance. This can be accomplished in a very simple manner, whether by thermal (heating to temperatures between 50 and 400° C., preferably between 100 and 200° C. or laser irradiation), photolytic (illumination, for example with wavelengths below 375 nm) or chemical (with organic or inorganic acids or bases) treatments of the solids containing the compounds according to the invention or of the solutions or dispersions containing the compounds according to the invention in organic or aqueous media, polymer solutions or melts. The aforementioned methods of conversion can also be combined. This makes possible the coloration of coatings, printing inks, particularly ink-jet and plastics, optionally in fiber form having unforeseeably improved properties, such as purity, color strength, brilliance and transparency, as well as interesting applications in analysis.

Accordingly, a further object of the invention is macromolecular material comprising in the mass a pigment of the formula (VII)

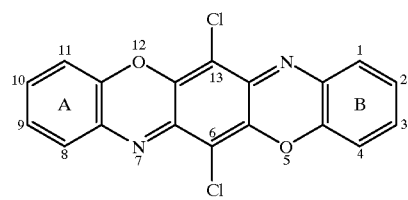

(VII)

wherein the nuclei designated A and B contain annelated rings as defined in formula (I), $R_1$ and $R_2$ have the meanings specified for the formula (I), and $R_3$ is hydrogen, produced in situ by thermal, photolytic or chemical degradation of a compound, of the formula (I)

as well as thermo-, photo- or chemosensitive recording material and also photo-, and electroluminescent materials comprising a compound according to the invention of the formula (I).

The examples hereinbelow illustrate the invention.

EXAMPLE 1

A suspension of 15 g of a compound of the formula

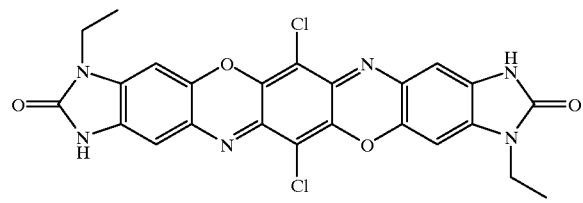

and 50 ml of N,N-dimethylformamide is mixed with 3 g of 4-dimethylaminopyridine. 12.9 g of di-tert-butyl dicarbonate are then added over 15 min. This mixture is stirred at room temperature in the absence of moisture. After 6 hours, another 12.9 g of di-tert-butyl dicarbonate are added and stirred in for a further 16 hours. The violet precipitate is filtered off, washed with 50 ml of N,N-dimethylformamide and 200 ml of methanol and then dried at room temperature under reduced pressure to leave 18.25 g of a product of the following formula:

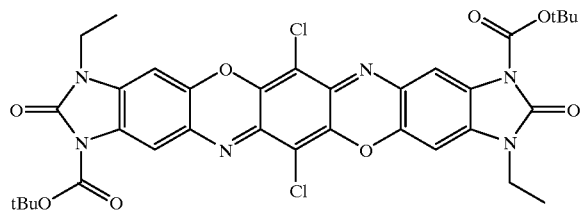

EXAMPLE 2

A suspension of 4.6 g of a compound of the formula

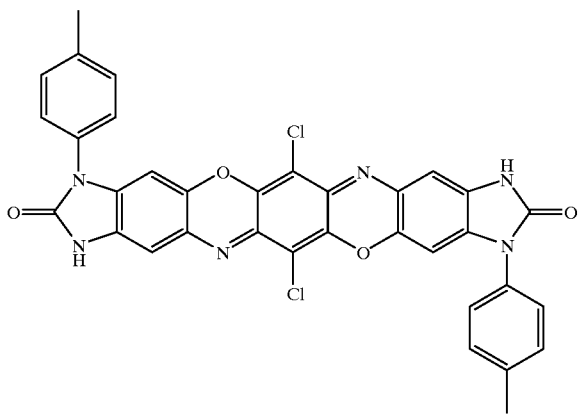

and 40 ml of N,N-dimethylfornamide is mixed with 1 g of 4-dimethylaminopyridine. 3.36 g of di-tert-butyl dicarbonate are then added over 15 min. This mixture is stirred at room temperature in the absence of moisture. After 6 hours, another 3.36 g of di-tert-butyl dicarbonate are added and stirred in for a further 16 hours. The violet precipitate is filtered off, washed with 50 ml of N,N-dimethylformamide and 100 ml of methanol and then dried at room temperature under reduced pressure to leave 4.75 g of a product of the following formula:

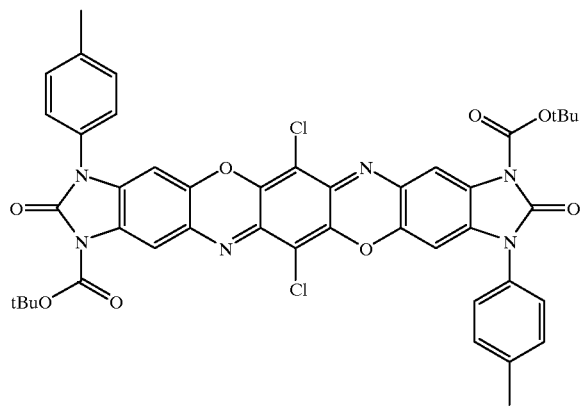

EXAMPLE 3

0.724 g of the product of Example 1 is heated in a test tube at 200° C. for 40 minutes. This gives 0.5 g of a blue powder (95% of theory). The analytical data of the powder correspond to those of pure diimidazolone (4,5-b;4',5'-m) triphendioxazine-3,11-diethyl-6,14-dichloro-2,10-dione.

EXAMPLE 4

A mixture of 3.62 g of the product of Example 1 and 11.4 g of toluene-4-sulfonic acid monohydrate in 75 ml of N,N-dimethylacetamide is heated to 130° C. with stirring, stirred at 130° C. for 4 hours and then allowed to cool down to room temperature. The precipitated pigment is filtered off, washed first with 25 ml of N,N-dimethylacetamide and then with 75 ml of methanol, and dried at 90° C. under reduced pressure to leave 2.4 g of a blue powder. The analytical data of the powder correspond to those of pure diimidazolone (4,5-b;4',5'-m) triphendioxazine-3,11-diethyl-6,14-dichloro-2,10-dione. The yield of the conversion is 92%.

Use Example 1

4 parts of the pigment of Example 1 are ball-milled with 96 parts of a mixture of 50 parts of a 60 percent solution of cocoaldehyde/melamine resin solution in butanol, 10 parts of xylene and 10 parts of ethylene glycol monoethyl ether for 24 hours. The resulting dispersion is sprayed onto aluminum sheet, air dried for 30 minutes and then baked at 120° C. for 30 minutes. This gives a film having a violet color and very good migration fastness and also good light and weather stability.

Use Example 2

Example of the production of a 0.1% colored PVC film (color pigment reduced 1:5 with white pigment):

16.5 parts of a plasticizer mixture consisting of equal parts of dioctyl phthalate and dibutyl phthalate are mixed with 0.05 part of the pigment of Example 2 and 0.25 part of titanium dioxide. Then 33.5 parts of polyvinyl chloride are added. The mixture is friction rolled for 10 minutes on a two-roll mill, the hide which forms being continually divided with a spatula and rolled up. One of the rolls is maintained at a temperature of 40° C. and the other at a temperature of 140° C. The mixture is then pulled off in the form of a hide and pressed between two polished metal platens at 160° C. for 5 minutes. The result obtained is a violet PVC film of high brilliance and very good migration and light fastness.

What is claimed is:
1. A compound of formula (I)

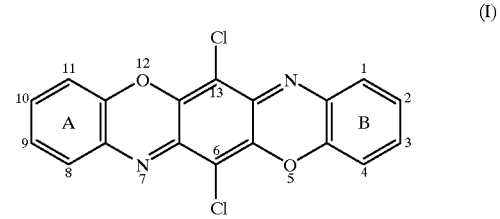

wherein nuclei designated A and B independently of each other comprise annelated rings which are fused on linearly, in 2,3- and 9,10-position, or angularly, in 1,2- and 8,9-position or in 3,4- and 10,11-position, selected from the group of formulae (a) to (p):

(a)
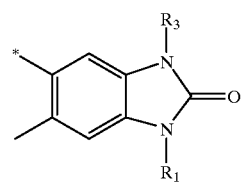
(b)
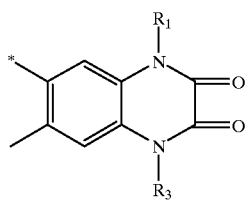
(c)
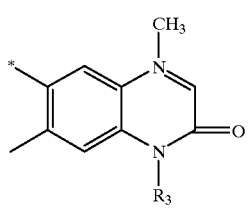
(d)
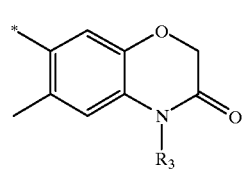
(e)
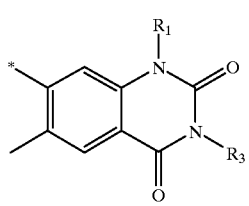
(f)
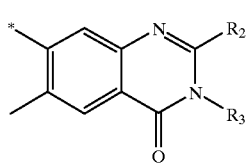
(g)
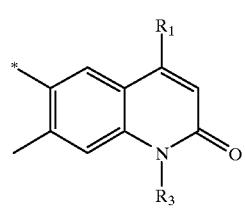
(h)
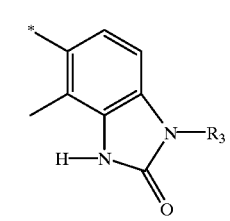
-continued
(i)
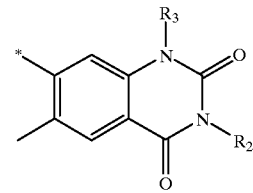
(j)
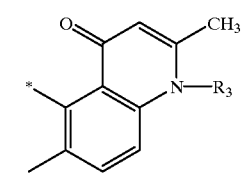
(k)
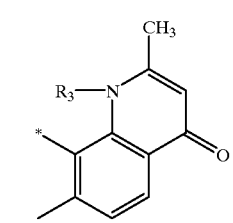
(l)
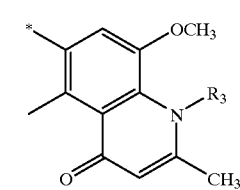
(m)
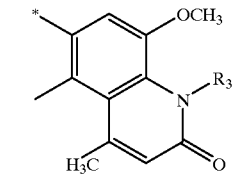
(n)
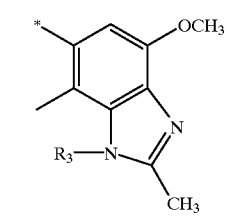
(o)
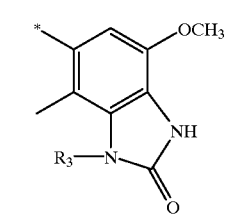

-continued (p)

wherein
- R₁ is hydrogen, $C_{1-8}$alkyl, unsubstituted phenyl or phenyl radical which is mono- or poly-substituted by radicals selected from the group consisting of halogen, nitro groups, $C_{1-8}$alkyl and $C_{1-2}$alkoxy,
- R₂ is hydrogen, $C_{1-8}$alkyl, unsubstituted phenyl, an amino group or phenyl which is mono- or poly-substituted by radicals selected from the group consisting of halogen, nitro groups, $C_{1-8}$alkyl and $C_{1-2}$alkoxy,
- an * designates a bond which leads to the nitrogen atom and the angular molecules in 3- and 10-position or in 2- and 9-position may each bear a $C_{1-2}$alkoxy group,
- R₃ is selected from the group consisting of formulae (II), (III) and (IV)

(II)

(III)

(IV)

wherein
m, n and p are independently of each other zero or 1;
X is $C_{1-4}$alkylene or $C_{2-8}$-alkenylene;
Y is a group —V—$(CH_2)_q$—;
Z is a group —V—$(CH_2)_r$—;
V is $C_{3-6}$cycloalkylene;
q is an integer from 1 to 6; and
r is an integer from 0 to 6;
R₄ and R₅ are independently hydrogen, $C_{1-6}$alkyl, $C_{1-4}$alkoxy, halogen, —CN, —NO₂, phenyl or phenoxy which is unsubstituted or phenyl or phenoxy substituted by $C_{1-4}$alkyl, $C_{1-4}$alkoxy or halogen;
Q is hydrogen, —CN, Si(R₄)₃, a group C(R₈)(R₉)(R₁₀), wherein R₈, R₉ and R₁₀ are halogen, a group in which R₄ and R₅ are as defined above,
a group —SO₂—R₁₁ or —SR₁₁, where R₁₁ is $C_{1-4}$alkyl,
a group —CH(R₁₂)₂, where R₁₂ is unsubstituted phenyl substituted by $C_{1-4}$alkyl, $C_{1-4}$alkoxy or halogen, or a group of the following formulae R₆ and R₇ are independently of each other hydrogen, $C_{1-8}$alkyl, a group of formula in which
X, Y, R₄, R₅, m and n are as defined above, or
R₆ and R₇ together with the nitrogen atom to which they are bonded form a pyrrolidinyl, piperidinyl or morpholinyl radical, with the proviso that, when R₃ is a group of formula (III), Q is hydrogen and n is zero, then m shall be 1 and X shall be a $C_{2-14}$alkylene or $C_{2-18}$alkenylene group which is branched at the carbon which is attached to the oxygen.

2. The compound according to claim 1, wherein R₁ is chlorine or $C_{1-4}$alkyl.

3. The compound according to claim 1, wherein R₂ is chlorine or $C_{1-4}$alkyl.

4. The compound according to claim 1, wherein R₃ is a group of formulae (V), (VI) or (IV)

(V)

(VI)

(IV)

wherein
m is zero or 1,
X is $C_{1-4}$alkylene or $C_{2-5}$alkenylene, $R_4$ and $R_5$ are independently of each other hydrogen, $C_{1-4}$alkyl, methoxy, chlorine or —NO$_2$, and Q is hydrogen, CN, CCl$_3$, a group

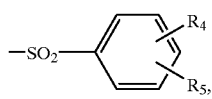

—SO$_2$CH$_3$ or —SCH$_3$, $R_6$ and $R_7$ are independently of each other hydrogen, $C_{1-4}$alkyl or a group

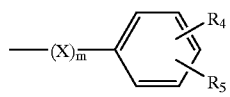

or $R_6$ and $R_7$ form together a piperidinyl radical,
with the proviso that, when $R_3$ is a group of the formula (VI) and Q is hydrogen, then X is

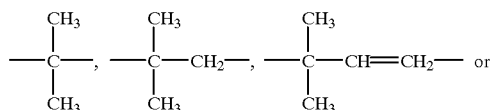

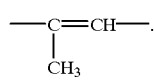

5. The compound according to claim 1, wherein $R_3$ is

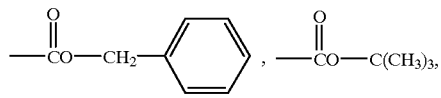

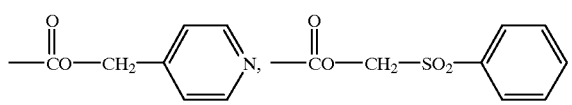

or

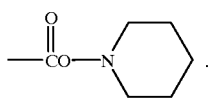

6. A process for preparing a compound of formula (I)

(I)

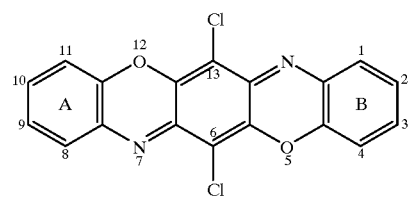

wherein nuclei designated A and B independently of each other comprise annelated rings which are fused on linearly, in 2,3- and 9,10-position, or angularly, in 1,2- and 8,9-position or in 3,4- and 10,11-position, selected from the group of formulae (a) to (p):

(a)
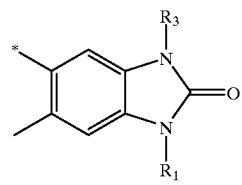

(b)
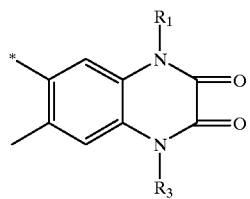

(c)
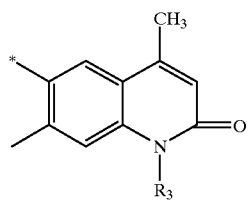

(d)
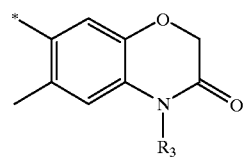

(e)
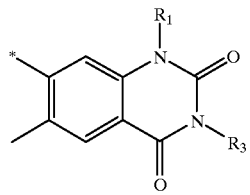

(f)
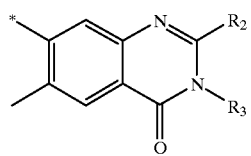

(g)
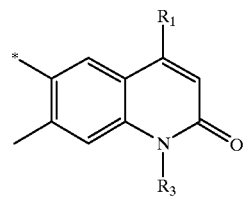

-continued (h) 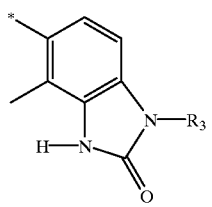

(i) 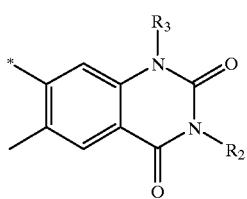

(j) 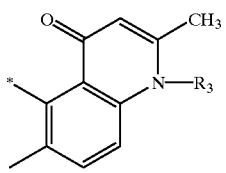

(k) 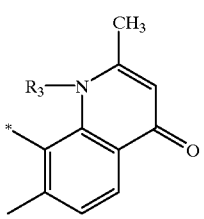

(l) 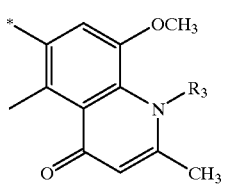

(m) 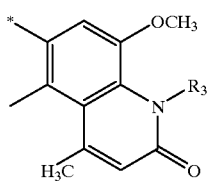

(n) 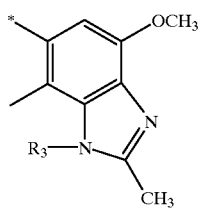

-continued (o) 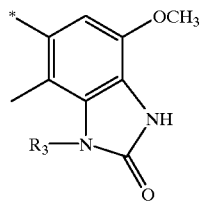

(p) 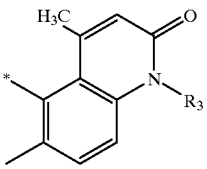

wherein $R_1$ is hydrogen, $C_{1-8}$alkyl, unsubstituted phenyl or phenyl radical which is mono- or poly-substituted by radicals selected from the group consisting of halogen, nitro groups, $C_{1-8}$alkyl and $C_{1-2}$alkoxy, $R_2$ is hydrogen, $C_{1-8}$alkyl, unsubstituted phenyl, an amino group or phenyl which is mono- or poly-substituted by radicals selected from the group consisting of halogen, nitro groups, $C_{1-8}$alkyl and $C_{1-2}$alkoxy, an * designates a bond which leads to the nitrogen atom and the annular molecules in 3- and 10-position or in 2- and 9-position may each bear a $C_{1-2}$alkoxy group, $R_3$ is selected from the group consisting of formulae (II), (III) and (IV)

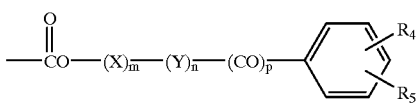  (II)

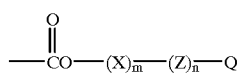  (III)

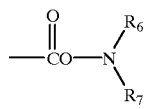  (IV)

wherein m, n and p are independently of each other zero or 1;

X is $C_{1-14}$alkylene or $C_{2-8}$alkenylene;

Y is a group —V—$(CH_2)_q$—;

z is a group —V—$(CH_2)_r$—;

V is $C_{3-6}$cycloalkylene;

q is an integer from 1 to 6; and r is an integer from 0 to 6;

$R_4$ and $R_5$ are independently hydrogen, $C_{1-6}$alkyl, $C_{1-4}$alkoxy, halogen, —CN, —$NO_2$, phenyl or phenoxy which is unsubstituted or phenyl or phenoxy substituted by $C_{1-4}$alkyl, $C_{1-4}$alkoxy or halogen;

Q is hydrogen, —CN, $Si(R_4)_3$, a group $C(R_8)(R_9)(R_{10})$, wherein $R_8$, $R_9$ and $R_{10}$ are halogen, a group

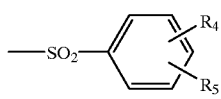

in which $R_4$ and $R_5$ are as defined above, a group $—SO_2—R_{11}$ or $—SR_{11}$, where $R_{11}$ is $C_{1-4}$alkyl, a group $—CH(R_{12})_2$, wherein $R_{12}$ is unsubstituted phenyl or phenyl substituted by $C_{1-4}$alkyl, $C_{1-4}$alkoxy or halogen, or a group of the following formulae

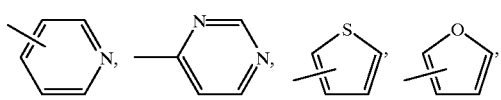

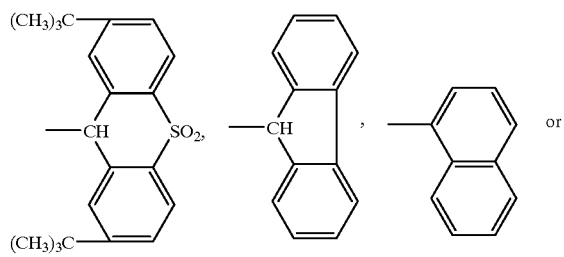

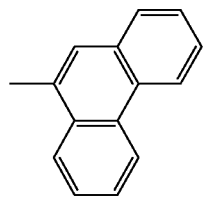

$R_6$ and $R_7$ are independently of each other hydrogen, $C_{1-18}$alkyl, a group of formula

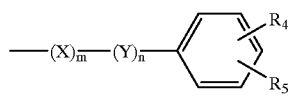

in which

X, Y, $R_4$, $R_5$, m and n are as defined above, or $R_6$ and $R_7$ together with the nitrogen atom to which they are bonded form a pyrrolidinyl, piperidinyl or morpholinyl radical, with the proviso that, when $R_3$ is a group of formula (III), Q is hydrogen and n is zero, then m shall be 1 and X shall be a $C_{2-14}$alkylene or $C_{2-8}$alkenylene group which is branched at the carbon which is attached to the oxygen, the process comprising:

reacting a triphendioxazine compound of formula (VII)

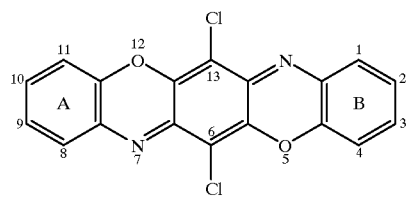

(VII)

wherein nuclei A and B are as defined in formula (I) except $R_3$ is hydrogen, in a desired molar ratio with a dicarbonate of formula (VIII)

$$R_3—O—R_3 \quad (VIII)$$

or with a trihaloacetic ester of formula (IX)

$$(R_{13})_3C—R_3 \quad (IX)$$

or with a 1:1 mixture of a dicarbonate of formula (VIII) and a dicarbonate of formula (X)

$$R'_3—O—R'_3 \quad (X)$$

or with a 1:1 mixture of a trihaloacetic ester of formula (IX) and a trihaloacetic ester of formula (XI)

$$(R_{13})_3C—R'_3 \quad (XI)$$

or with an azide of formula (XII)

$$R_3N_3 \quad (XII)$$

which may also be used in a 1:1 mixture with $$R'_3N_3 \quad (XIII)$$

or with a carbonate of formula (XIV)

$$R_3—OR_{14} \quad (XIV)$$

which may also be used in a 1:1 mixture with $$R'_3—OR_{14} \quad (XV)$$

or with an alkylideneiminooxyformic ester of formula (XVI)

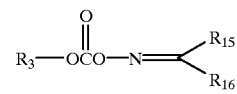

(XVI)

which may also be used in a 1:1 mixture with (XVII)

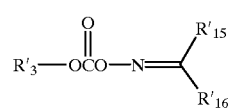

wherein $R_3$ is defined as in formula (I) and $R'_3$ has a meaning of $R_3$ which is different from $R_3$, $R_{13}$ is chlorine, fluorine or bromine, $R_{14}$ is $C_{1-4}$alkyl, unsubstituted phenyl or phenyl substituted by halogen, $C_{1-4}$alkyl, $C_{1-4}$alkoxy or —CN, $R_{15}$ is —CN or —COOR$_{14}$, and $R_{16}$ is unsubstituted phenyl or phenyl substituted by halogen, C$_{1-4}$alkyl, C$_{1-4}$alkoxy or —CN, R'$_{15}$ and R'$_{16}$ each have a meaning of R$_{15}$ and R$_{16}$, respectively, which is different therefrom, in an aprotic organic solvent in the presence of a base as catalyst.

7. A macromolecular organic material comprising in the mass as a pigment a compound of formula (I) as claimed in claim 1.

8. A macromolecular organic material comprising in the mass a compound of formula (VII)

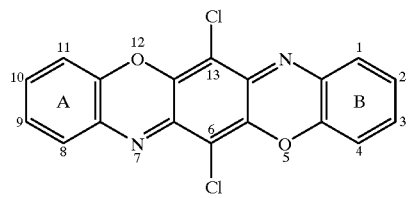

(VII)

wherein nuclei designated A and B, are as defined in claim 1,

R$_1$ and R$_2$ are as defined for the formula (I), and

R$_3$ is hydrogen, which is produced in situ by thermal, photolytic or chemical degradation of a compound of formula (I) according to claim 1.

9. A thermo-, photo- or chemosensitive recording material comprising a compound of the formula (I) according to claim 1.

10. A photo- and electroluminescent material comprising a compound of the formula (I) according to claim 1.

* * * * *